United States Patent
Sun et al.

(10) Patent No.: US 9,879,276 B2
(45) Date of Patent: Jan. 30, 2018

(54) DROUGHT TOLERANCE ASSOCIATED PROTEIN DT1 AND CODING SEQUENCE AND APPLICATION THEREOF

(75) Inventors: Chuanqing Sun, Beijing (CN); Xia Zhang, Beijing (CN); Fengxia Liu, Beijing (CN); Na Wang, Beijing (CN); Zhen Su, Beijing (CN); Lubin Tan, Beijing (CN); Zuofeng Zhu, Beijing (CN); Yongcai Fu, Beijing (CN); Daoxin Xie, Beijing (CN)

(73) Assignee: China Agricultural University, Beijing (CN)

( * ) Notice: Subject to any disclaimer, the term of this patent is extended or adjusted under 35 U.S.C. 154(b) by 930 days.

(21) Appl. No.: 14/116,759

(22) PCT Filed: May 9, 2012

(86) PCT No.: PCT/CN2012/075230
§ 371 (c)(1),
(2), (4) Date: Feb. 6, 2014

(87) PCT Pub. No.: WO2012/152216
PCT Pub. Date: Nov. 15, 2012

(65) Prior Publication Data
US 2015/0135361 A1 May 14, 2015

(30) Foreign Application Priority Data

May 10, 2011 (CN) .......................... 2011 1 0119679
Sep. 27, 2011 (CN) .......................... 2011 1 0296327

(51) Int. Cl.
| | | |
|---|---|---|
| C12N 15/29 | (2006.01) | |
| C12N 15/82 | (2006.01) | |
| C07K 14/415 | (2006.01) | |
| C12Q 1/68 | (2006.01) | |

(52) U.S. Cl.
CPC ........ *C12N 15/8273* (2013.01); *C07K 14/415* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 2003/0236208 A1* | 12/2003 | Kmiec | ................. | C12N 15/102 514/44 R |
| 2009/0093620 A1* | 4/2009 | Kovalic | ............... | C07K 14/415 536/23.1 |

FOREIGN PATENT DOCUMENTS

CN          102094001 A          6/2011

OTHER PUBLICATIONS

Matsumoto et al. (Nature 436:793-800(2005)).*
Tanaka et al. (Genome Res. 17:175-183(2007)).*
Guo et al. (2004, Proc. Natl. Acad. Sci. USA 101: 9205-9210).*
Roberts et al. (GenBank Accession No:AF234296, submitted Feb. 15, 2000).*
Yang et al. "Overexpression of *SOS* (*Salt Overly Sensitive*) Genes Increases Salt Tolerance in Transgenic *Arabidopsis*" Molecular Plant 2(1):22-31 (2009).
Zhang et al. "Identification of a drought tolerant introgression line derived from Dongxiang common wild rice (*O. rufipogon* Griff.)" Plant Molecular Biology 62:247-259 (2006).
International Search Report and Written Opinion issued in corresponding PCT Application No. PCT/CN2012/075230, dated Aug. 2, 2012 (15 pages).
GenBank Database Accession NM_001185885 "*Oryza sativa* Japonica Group Os02g0163533 (Os02g0163533) mRNA, complete cds" Jun. 8, 2010.
GenBank Database Accession AK241536 "*Oryza sativa* Japonica Group cDNA, clone: J065173F08, full insert sequence" Dec. 4, 2008.
Zhang et al. "Identification of a drought intolerant introgression line derived from Dongxiang common wild rice (*O. rufipogon* griff.)" Plant Molecular Biology 62:247-259 (2006).

* cited by examiner

*Primary Examiner* — Elizabeth McElwain
*Assistant Examiner* — Charles Logsdon
(74) *Attorney, Agent, or Firm* — Myers Bigel, P.A.

(57) ABSTRACT

The present invention provides a drought tolerance associated protein, DT1, a nucleic acid molecule encoding the DT1 protein and application thereof.

16 Claims, No Drawings

SEQUENCE LISTING

<160> NUMBER OF SEQ ID NOS: 14

<210> SEQ ID NO 1
<211> LENGTH: 140
<212> TYPE: PRT
<213> ORGANISM: Oryza rufipogon Griff.

<400> SEQUENCE: 1

```
Met Ala Ser Phe Ala Arg Ser Phe Leu Gly Cys Gly Gly Lys Ala Gly
1               5                   10                  15

Arg Ala Gly Ala Arg Arg Pro Arg Ala Leu Ser Ser Glu Val Arg Gly
            20                  25                  30

Gly Asp Leu Ser Gln Arg Lys Pro Ala Pro Gly Val His Glu Ala Gly
        35                  40                  45

Ser Gly Cys Val His Lys Asp Pro Tyr Pro Pro Leu Ser Glu Ala Ala
    50                  55                  60

Thr Lys Leu Asn Ala Leu Leu Asp Glu Ile Lys Gly Lys Lys Leu Asn
65                  70                  75                  80

Ser Val Pro Leu Val Met Val Gly Lys Thr Ile Ser Asn Phe Glu Ile
                85                  90                  95

Val Arg Glu Val His Phe Lys Asn Ile Gly Arg Ser Trp Ala Ile
            100                 105                 110

Thr Ala Val Leu Leu Gly Gly Tyr Phe Thr Gly Tyr Cys Met Glu Glu
            115                 120                 125

Glu Lys Thr Arg Lys Lys Arg Gln Ser Leu Val Asn
    130                 135                 140
```

<210> SEQ ID NO 2
<211> LENGTH: 693
<212> TYPE: DNA
<213> ORGANISM: Oryza rufipogon Griff.

<400> SEQUENCE: 2

```
agaaccccca acctaaccct gcagccgcga tcgctggcag cgaaagagag gagtgggcat      60
ggcttcgttt gcgcgatctt tcttgggctg cggcggcaag gcaggacgcg cgggcgctcg     120
ccgtccccgc gccctttctt ccgaggtccg cggcggcgat ctcagccagc gcaagccagc     180
tcctggcgtt cacgaggcag ggagcggatg cgtccacaag gatccgtatc ctcccctatc     240
tgaggcggcc accaagctaa atgcactgct ggatgaaatt aaggggaaga agctcaattc     300
cgtgccattg gtaatggtgg caaaaccat ttcaaacttt gaaattgttc ggagagaggt      360
tcacttcaaa aacatcggtc gatcatgggc cattaccgcc gttcttcttg gtggctactt     420
cactggctat tgtatggaag aggagaaaac caggaaaaaa aggcaatctt tagtgaatta     480
agaagcccgc ctgtagagga catatgtaag gtgtcccatg tgtgcaaatg tggaagtctc     540
tatctaatct agatctccct ttggatatgt taactgcact gtttgtttcc attcaactat     600
gctgatatct gttacattgt gatctggagg cagcattaga gttgtacatt tttattaact     660
acttgttata cttttggcct acgcatttca aca                                  693
```

<210> SEQ ID NO 3
<211> LENGTH: 3275
<212> TYPE: DNA
<213> ORGANISM: Oryza rufipogon Griff.

<400> SEQUENCE: 3

```
gtaagtccaa aattccccat acctctcgca ctccactcca gaaccccaa cctaaccctg      60 cagccgcgat cgctggcagc gaaagagagg agtgggcatg gcttcgtttg cgcgatcttt    120
cttgggctgc ggcggcaagg caggacgcgc gggcgctcgc cgtccccgcg ccctttcttc    180
cgaggtccgc ggcggcgatc tcagccagcg caagccagct cctggcgttc acgaggcagg    240
gagcggatgc gtccacaagg atccgtatcc tcccctatct gaggcggcca ccaaggtaat    300 cccgccccc aagttcgtta cagcagagga aagcttgttc ttcttcttct tcttcttctt    360
cttcttcttc ttcttcttct tcttcttctt cttcttcttc ttcttcttct tcttcttctt    420
cttctttccc tcttcgaaac caaatattgt atacgcgagt tgcagaacga cctgcaccct    480
gaaccctgaa tagatagata aaggtgttg ccttgaatgt tcttgatact gcaaattttg    540
ggggcaaatg tttcttttct tttctttttt gtggaagggg gtgggggttc tacttgttac    600 ttgatttta gataatgtct ttttacttga tgggaggcat catccattgt tcgctttaga    660
tcccgcaatc tctggttcg acccacgtaa tctagtcaat cttgaattat ccgttactgc    720
ttcattcctc tacatgcgtt ccctctcacc ataagcatcc aaatctgtgc caagtctttt    780
gttcagctca aggccttgtc ttgtcctcat cagcattctt ggtccagtaa gaattagtca    840
tggtgctgga attgttgttt ttggcaggct tgagtaggcc ctgtaaagtt gcaagtttgt    900
gtcttcccta gccctagttc ctttcctgtc attatttttg tgctattctg ttccttgata    960
tgtaaagagg tgtggttgct tgattatttt tccgatttca gacatcaagt tcattgttta   1020
tgattgaatc gctatgctg tgaaagtacc tttcttccag aattcatcat tttcttaacc   1080
cgttcttagg gcctcttgtt tgaacagtgc tattcatgat actgtagtat gcttaacttc   1140
cactgcgtat tttttgaact gatatttgaa atgcatggta tgatacatca caaacacctt   1200
aatgttatca aaccaaagg aaacaattcc ttatggtttg aattagctaa acggctaaac   1260
cttctggtgc tttttattcc gaacaaacat catttgccta tgtttcgtta cattgcagtt   1320
gctatcatat gcattccatt tggaactagc atgtgttctt taaaatattt tcttttttcg   1380
ttttcttttg ataagacaca ttcagagtca atttatccat agatgaaagt tctgcgccac   1440
aatatattat aaagtttgga ggatacaaac ccactttaga aaatactagt gtttccatgc   1500
caatttgtta gtttatactc cttcagcact agctacatct acatggagca ctatgtacat   1560
ctacatggag tactgataaa ttttgttaca aaatactgga gtacacatct acatgtgcat   1620
tctctataga gctctctgaa tatccttcag cactatcata tgctaccttc agttaaagaa   1680
aaacaactat tatttgttac ttttcaaagt aatcaaatgt cattttgtcc actaaatttt   1740
atttccataa tgcaagagtt atagatatgt gatttatgaa agtattgatt cgatctgtac   1800
caaatttacc agtaccattt tcatatgtcc aaattcatg ttgtaaacaa tatatttgat   1860
caaaattaat atggtttgcg tgtacacatg caattgcgac atgttttgt gtccgggggg   1920 agtacatatt atgtttggct tgtagttcc tttgatgatt gtattgcatc tggctgttgc   1980
cctcggtggt gtgatcactt cattctcttt gtttgatgca actacttaag tctgataggc   2040
atttataaac tcgtgtaaga agatcccaag cctctcacgt ttcagcatta ataaagagca   2100
tgtgaacaat atttcttctc agttgcacag attgtgcatt tgagcatatc aatgaccaga   2160
ccttttccat cttcatatcc ttcattattc tgttatatca gacttgatca aacaaccatg   2220
actgaataag atccttgatt gtatttgtta gtattctcta cgcgcattag gtgtagctgt   2280
atgctctctt atactagttt gttgttaggt cttctttagc acctgaaaaa aatcacggga   2340
```

| | | |
|---|---|---|
| tattttgcac agcgaaagcc ttgccctgtg taagaccatt tgacttaata tattcaggtg | 2400 | |
| gccatttcgc ccctcggtga accgtcaaaa aatatatatc ttttgttata gtcaagtgtg | 2460 | |
| gtctgatttg gtatgattaa attgttgata ttaacttatt catttgctca tgcctccatt | 2520 | |
| ggaaagttca tggtaaacac atattcattc tgtttattgg cgcttatgaa aatatgaaaa | 2580 | |
| tagttcttga gtggacattt ccgtgtcaag atctgtggtc attttttcgg cctgcgcatg | 2640 | |
| caactaggtg gttataggtg tttgttggat ggtacatgtt tcatactgcg ttttagttcc | 2700 | |
| atatctagta cgataaacca gatggaacat gctttatttg atggatgcta ttcttttttt | 2760 | |
| tttcagctaa atgcactgct ggatgaaatt aaggggaaga agctcaattc cgtgccattg | 2820 | |
| gtaatggtgg gcaaaaccat ttcaaagtgc gtgcatattc ccctgtttcc atttcatacc | 2880 | |
| tgtttgaatc acagctcaaa cgatttccat gtttgtttgt agctttgaaa ttgttcggag | 2940 | |
| agaggttcac ttcaaaaaca tcggtcgatc atgggccatt accgccgttc ttcttggtgg | 3000 | |
| ctacttcact ggctattgta tggaagagga gaaaaccagg aaaaaaaggc aatctttagt | 3060 | |
| gaattaagaa gcccgcctgt agaggacata tgtaaggtgt cccatgtgtg caaatgtgga | 3120 | |
| agtctctatc taatctagat ctcccttttgg atatgttaac tgcactgttt gtttccattc | 3180 | |
| aactatgctg atatctgtta cattgtgatc tggaggcagc attagagttg tacattttta | 3240 | |
| ttaactactt gttatacttt tggcctacgc atttc | 3275 | |

```
<210> SEQ ID NO 4
<211> LENGTH: 5
<212> TYPE: PRT
<213> ORGANISM: Artificial
<220> FEATURE:
<223> OTHER INFORMATION: Poly-Arg tag sequence

<400> SEQUENCE: 4

Arg Arg Arg Arg Arg
1               5

<210> SEQ ID NO 5
<211> LENGTH: 6
<212> TYPE: PRT
<213> ORGANISM: Artificial
<220> FEATURE:
<223> OTHER INFORMATION: Poly-His tag sequence

<400> SEQUENCE: 5

His His His His His His
1               5

<210> SEQ ID NO 6
<211> LENGTH: 8
<212> TYPE: PRT
<213> ORGANISM: Artificial
<220> FEATURE:
<223> OTHER INFORMATION: FLAG tag sequence

<400> SEQUENCE: 6

Asp Tyr Lys Asp Asp Asp Asp Lys
1               5

<210> SEQ ID NO 7
<211> LENGTH: 8
<212> TYPE: PRT
<213> ORGANISM: Artificial
<220> FEATURE:
<223> OTHER INFORMATION: Strep-tag II sequence
```

<400> SEQUENCE: 7

Trp Ser His Pro Gln Phe Glu Lys
1               5

<210> SEQ ID NO 8
<211> LENGTH: 10
<212> TYPE: PRT
<213> ORGANISM: Artificial
<220> FEATURE:
<223> OTHER INFORMATION: c-myc tag sequence

<400> SEQUENCE: 8

Glu Gln Lys Leu Ile Ser Glu Glu Asp Leu
1               5                   10

<210> SEQ ID NO 9
<211> LENGTH: 26
<212> TYPE: DNA
<213> ORGANISM: Artificial
<220> FEATURE:
<223> OTHER INFORMATION: PCR primer

<400> SEQUENCE: 9
agaaccccca acctaaccgg ctgcag                                    26

<210> SEQ ID NO 10
<211> LENGTH: 31
<212> TYPE: DNA
<213> ORGANISM: Artificial
<220> FEATURE:
<223> OTHER INFORMATION: PCR primer

<400> SEQUENCE: 10
ggactagtct ctaatgctgc ctccagatca c                              31

<210> SEQ ID NO 11
<211> LENGTH: 22
<212> TYPE: DNA
<213> ORGANISM: Artificial
<220> FEATURE:
<223> OTHER INFORMATION: PCR primer

<400> SEQUENCE: 11
gccaccaagc taaatgcact gc                                        22

<210> SEQ ID NO 12
<211> LENGTH: 23
<212> TYPE: DNA
<213> ORGANISM: Artificial
<220> FEATURE:
<223> OTHER INFORMATION: PCR primer sequence

<400> SEQUENCE: 12
ctctaatgct gcctccagat cac                                       23

<210> SEQ ID NO 13
<211> LENGTH: 18
<212> TYPE: DNA
<213> ORGANISM: Artificial
<220> FEATURE:
<223> OTHER INFORMATION: PCR primer

<400> SEQUENCE: 13
tacttctaca cagccatc                                             18

```
<210> SEQ ID NO 14
<211> LENGTH: 18
<212> TYPE: DNA
<213> ORGANISM: Artificial
<220> FEATURE:
<223> OTHER INFORMATION: PCR primer

<400> SEQUENCE: 14
cgtctgtcga gaagtttc                                                 18
```

DROUGHT TOLERANCE ASSOCIATED PROTEIN DT1 AND CODING SEQUENCE AND APPLICATION THEREOF

STATEMENT OF RELATED APPLICATIONS

This application claims priority to Chinese Patent Application CN 201110119679, filed May 10, 2011 and Chinese Patent Application No. CN 201110296327, filed Sep. 27, 2011, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 9207-82TS SUBSTITUTE ST25.txt, 9,091 bytes in size, generated on Jun. 3, 2014 and filed via EFS-Web, is provided in lieu of a paper copy. This Sequence Listing is incorporated by reference into the specification for its disclosures.

FIELD OF THE INVENTION

The present invention relates to a drought tolerance associated protein DT1 and coding gene and application thereof.

BACKGROUND OF THE INVENTION

Shortage of water resources is becoming an important factor for restricting agricultural development in China and even the world. The current water resource share per capita in China is only ¼ of the world level per capita and water shortage has become one of the main obstacles faced by industrial and agricultural production in China. It is important to cultivate species tolerant to drought in the breeding of multiple crops. For example, rice is one of the most important alimentary crops in China, with its total yield around 40% of the total yield of food crops; while at the same time, it is a crop that has a requirement for a large amount of water. The increasingly draconic shortage of water resources has become an important issue faced by rice producers. It is advantageous to cultivate rice species tolerant to drought in order to realize high yield and stable production of rice under limited water resources. It is further of practical significance to study the genetic basis for drought tolerance of rice, and to strengthen the identification and utilization of drought tolerance gene resources of *Oryza*.

Common wild rice (*O. rufipogon* Griff.), as the ancestor of the cultivated rice (*O. sativa* L.), is an important gene bank for genetic improvement of cultivated rice. Since the evolution of wild rice into cultivated rice, not only have many agronomic characteristics been greatly changed, but also genetic diversity has been reduced and the number of alleles has decreased, e.g., it has been shown that the numbers of alleles found in cultivated rice is only 60% of wild rice.

Jiangxi Dongxiang wild rice (*O. rufipogon* Griff.), which has a reputation of being a "plant panda," is presently the wild rice having the most northerly (28° 14' N) habitat in the world, having good isolation conditions away from cultivated rice, having no gene introgression from cultivated rice and having the properties of low temperature tolerance and drought tolerance. It is of significant importance for rice production to identify and clone drought tolerance associated genes from wild rice.

SUMMARY OF THE INVENTION

The present invention is based, in part, on the discovery of a drought tolerance associated protein DT1 and coding sequence and application thereof. The protein provided by the present invention is called DT1 protein, originating from *Oryza* common wild rice (*O. rufipogon* Griff).

Thus, in one embodiment, the present invention provides a protein (e.g., an isolated protein) comprising an amino acid sequence selected from the group consisting of: a) the amino acid sequence of SEQ ID NO:1; b) an amino acid sequence having at least 80% identity with the amino acid sequence of SEQ ID NO:1 and is a DT1 protein; c) a fragment of at least 15 contiguous amino acids of the amino acid sequence of SEQ ID NO:1; and d) an amino acid sequence of a naturally occurring allelic variant of a DT1 protein.

Further provided herein is a nucleic acid molecule (e.g., an isolated nucleic acid molecule) selected from the group consisting of: a) the nucleotide sequence of SEQ ID NO:2; b) a nucleotide sequence that encodes the amino acid sequence of SEQ ID NO:1; c) a nucleotide sequence that encodes at least 15 contiguous amino acids of the amino acid sequence of SEQ ID NO:1; d) a nucleotide sequence having at least 80% identity with the nucleotide sequence of SEQ ID NO:2 and that encodes a DT1 protein; e) a nucleotide sequence that encodes a naturally occurring allelic variant of a polypeptide having the amino acid sequence of SEQ ID NO:1; f) a nucleotide sequence that encodes an amino acid sequence having at least 80% identity with the amino acid sequence of SEQ ID NO:1 and is a DT1 protein; g) a nucleotide sequence consisting of nucleotides 59 through 481 of the nucleotide sequence of SEQ ID NO:2; h) a nucleotide sequence consisting of nucleotides 19 through 641 of the nucleotide sequence of SEQ ID NO:2; i) a nucleotide sequence that differs from the nucleotide sequence of (a)-(f), above due to the degeneracy of the genetic code and that encodes a DT1 protein; and i) a nucleotide sequence that hybridizes with the complement of the nucleotide sequence of (a)-(c) above under stringent conditions.

The present invention further provides a method of producing a transgenic plant having increased drought tolerance, comprising introducing a nucleic acid molecule and/or vector of this invention into a cell of a plant under conditions whereby the nucleic acid molecule is expressed to produce a DT1 protein, thereby producing a transgenic plant having increased drought tolerance.

DETAILED DESCRIPTION OF THE INVENTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed.

Definitions

The terminology used in the description of the invention herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

As used in the description of the invention and the appended claims, the singular forms "a", "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value such as an amount, concentration, time period and the like, is meant to encompass variations of ±20%, ±10%, ±5%, ±1%, ±0.5%, or even ±0.1% of the specified amount.

"Yield" as used herein refers to the production of a commercially and/or agriculturally important plant, plant biomass (e.g., dry biomass), plant part (e.g., roots, tubers, seed, leaves, fruit, flowers), plant material (e.g., an extract) and/or other product produced by the plant (e.g., a recombinant polypeptide). In some embodiments of the present invention, "increased yield" is assessed in terms of an increase in plant growth (e.g., height and/or width) or an increase in the rate of plant growth.

The term "modulate" (and grammatical variations) refers to an increase or decrease.

As used herein, the terms "increase," "increases," "increased," "increasing," enhance," "enhances," "enhanced," "enhancing" and similar terms indicate an elevation of at least about 5%, 10%, 25%, 50%, 75%, 100%, 150%, 200%, 300%, 400%, 500% or more as compared to a control.

As used herein, the terms "reduce," "reduces," "reduced," "reduction" and similar terms refer to a decrease of at least about 5%, 10%, 25%, 35%, 50%, 75%, 80%, 85%, 90%, 95%, 97% or more as compared to a control. In particular embodiments, the reduction results in no or essentially no (i.e., an insignificant amount, e.g., less than about 10% or even 5%) detectable activity or amount.

A "promoter" is a nucleotide sequence that controls or regulates the transcription of a nucleotide sequence (i.e., a coding sequence) that is operatively associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

The term "promoter" can also refer to a region of a nucleotide sequence that incorporates the necessary signals for the efficient expression of a coding sequence. This may include sequences to which an RNA polymerase binds, but is not limited to such sequences and can include regions to which other regulatory proteins bind together with regions involved in the control of protein translation and can also include coding sequences.

Furthermore, a "plant promoter" of this invention is a promoter capable of initiating transcription in plant cells. Such promoters include those that drive expression of a nucleotide sequence constitutively, those that drive expression when induced, and those that drive expression in a tissue- or developmentally-specific manner, as these various types of promoters are known in the art.

Thus, for example, in some embodiments of the invention, a constitutive promoter can be used to drive the expression of a transgene of this invention in a plant cell. A constitutive promoter is an unregulated promoter that allows for continual transcription of its associated gene or coding sequence. Thus, constitutive promoters are generally active under most environmental conditions, in most or all cell types and in most or all states of development or cell differentiation.

Any constitutive promoter functional in a plant can be utilized in the instant invention. Exemplary constitutive promoters include, but are not limited to, the promoters from plant viruses including, but not limited to, the 35S promoter from CaMV (Odell et al., *Nature* 313: 810(1985)); figwort mosaic virus (FMV) 35S promoter (P-FMV35S, U.S. Pat. Nos. 6,051,753 and 6,018,100); the enhanced CaMV35S promoter (e35 S); the 1'- or 2'-promoter derived from T-DNA of *Agrobacterium tumefaciens*; the nopaline synthase (NOS) and/or octopine synthase (OCS) promoters, which are carried on tumor-inducing plasmids of *Agrobacterium tumefaciens* (Ebert et al., *Proc. Natl. Acad. Sci.* (U.S.A.), 84:5745 5749, 1987); actin promoters including, but not limited to, rice actin (McElroy et al., *Plant Cell* 2: 163 (1990); U.S. Pat. No. 5,641,876); histone promoters; tubulin promoters; ubiquitin and polyubiquitin promoters, including a corn ubiquitin promoter or a rice ubiquitin promoter ((Sun and Callis, *Plant J.,* 11(5):1017-1027 (1997)); Christensen et al., *Plant Mol. Biol* 12: 619 (1989) and Christensen et al., *Plant Mol. Biol.* 18: 675(1992)); pEMU (Last et al., *Theor Appl. Genet.* 81: 581(1991)); the mannopine synthase promoter (MAS) (Velten et al., *EMBO J.* 3: 2723(1984)); maize H3 histone promoter (Lepelit et al., *Mol. Gen. Genet.* 231: 276 (1992) and Atanassova et al., *Plant Journal* 2: 291 (1992)); the ALS promoter, a Xba1/Nco1 fragment 5' to the *Brassica napus* ALS3 structural gene (or a nucleotide sequence that has substantial sequence similarity to said Xba1/Nco1 fragment); ACT11 from *Arabidopsis* (Huang et al., *Plant Mol. Biol.* 33:125-139 (1996)); Cat3 from *Arabidopsis* (GenBank No. U43147, Zhong et al., *Mol. Gen. Genet.* 251:196-203 (1996)); GPc1 from maize (GenBank No. X15596, Martinez et al., *J. Mol. Biol.* 208: 551-565 (1989)); and Gpc2 from maize (GenBank No. U45855, Manjunath et al., *Plant Mol. Biol.* 33:97-112 (1997)), including any combination thereof.

In some embodiments of the present invention, an inducible promoter can be used to drive the expression of a transgene. Inducible promoters activate or initiate expression only after exposure to, or contact with, an inducing agent. Inducing agents include, but are not limited to, various environmental conditions (e.g., pH, temperature), proteins and chemicals. Examples of environmental conditions that can affect transcription by inducible promoters include pathogen attack, anaerobic conditions, extreme temperature and/or the presence of light. Examples of chemical inducing agents include, but are not limited to, herbicides, antibiotics, ethanol, plant hormones and steroids. Any inducible promoter that is functional in a plant can be used in the instant invention (see, Ward et al., (1993) *Plant Mol. Biol.* 22: 361 (1993)). Exemplary inducible promoters include, but are not limited to, promoters from the ACEI system, which respond to copper (Melt et al., *PNAS* 90: 4567 (1993)); the ln2 gene from maize, which responds to benzenesulfonamide herbicide safeners (Hershey et al., (1991) *Mol. Gen. Genetics* 227: 229 (1991) and Gatz et al., *Mol. Gen. Genetics* 243: 32 (1994)); a heat shock promoter, including, but not limited to, the soybean heat shock promoters Gmhsp 17.5-E, Gmhsp 17.2-E and Gmhsp 17.6-L and those described in U.S. Pat. No. 5,447,858; the Tet repressor from Tn10 (Gatz et al., *Mol. Gen. Genet.* 227: 229 (1991)) and the light-inducible promoter from the small subunit of ribulose bisphosphate carboxylase (ss-RUBISCO), including any combination thereof. Other examples of inducible promoters include, but are not limited to, those described by Moore et al. (*Plant J.* 45:651-683 (2006)). Additionally, some inducible promoters respond to an inducing agent to which plants do not normally respond. An example of such an inducible promoter is the inducible promoter from a steroid hormone gene, the transcriptional activity of which is induced by a glucocorticosteroid hormone (Schena et al., *Proc. Natl. Acad. Sci. U.S.A.* 88: 421 (1991)).

In further embodiments of the present invention, a tissue-specific promoter can be used to drive the expression of a transgene in a particular tissue in the transgenic plant. Tissue-specific promoters drive expression of a nucleic acid only in certain tissues or cell types, e.g., in the case of plants, in the leaves, stems, flowers and their various parts, roots, fruits and/or seeds, etc. Thus, plants transformed with a nucleic acid of interest operably linked to a tissue-specific promoter produce the product encoded by the transgene exclusively, or preferentially, in a specific tissue or cell type.

Any plant tissue-specific promoter can be utilized in the instant invention. Exemplary tissue-specific promoters include, but are not limited to, a root-specific promoter, such as that from the phaseolin gene (Murai et al., *Science* 23: 476 (1983) and Sengupta-Gopalan et al., *Proc. Natl. Acad. Sci. USA* 82: 3320 (1985)); a leaf-specific and light-induced promoter such as that from cab or rubisco (Simpson et al. *EMBO J.* 4: 2723 (1985) and Timko et al., *Nature* 318: 579 (1985)); the fruit-specific E8 promoter from tomato (Lincoln et al. *Proc. Nat'l. Acad. Sci. USA* 84: 2793-2797 (1988); Deikman et al. *EMBO J.* 7: 3315-3320 (1988); Deikman et al. *Plant Physiol.* 100: 2013-2017 (1992); seed-specific promoters of, for example, *Arabidopsis thaliana* (Krebbers et al. (1988) *Plant Physiol.* 87:859); an anther-specific promoter such as that from LAT52 (Twell et al. *Mol. Gen. Genet.* 217: 240 (1989)) or European Patent Application No 344029, and those described by Xu et al. (*Plant Cell Rep.* 25:231-240 (2006)) and Gomez et al. (*Planta* 219:967-981 (2004)); a pollen-specific promoter such as that from Zm13 (Guerrero et al., *Mol. Gen. Genet.* 224: 161 (1993)), and those described by Yamaji et al. (*Plant Cell Rep.* 25:749-57 (2006)) and Okada et al. (*Plant Cell Physiol.* 46:749-802 (2005)); a pith-specific promoter, such as the promoter isolated from a plant TrpA gene as described in International PCT Publication No. WO93/07278; and a microspore-specific promoter such as that from apg (Twell et al. *Sex. Plant Reprod.* 6: 217 (1993)). Exemplary green tissue-specific promoters include the maize phosphoenol pyruvate carboxylase (PEPC) promoter, small subunit ribulose bis-carboxylase promoters (ssRUBISCO) and the chlorophyll a/b binding protein promoters, including any combination thereof.

A promoter of the present invention can also be developmentally specific in that it drives expression during a particular "developmental phase" of the plant. Thus, such a promoter is capable of directing selective expression of a nucleotide sequence of interest at a particular period or phase in the life of a plant (e.g., seed formation), compared to the relative absence of expression of the same nucleotide sequence of interest in a different phase (e.g. seed germination). For example, in plants, seed-specific promoters are typically active during the development of seeds and germination promoters are typically active during germination of the seeds. Any developmentally-specific promoter capable of functioning in a plant can be used in the present invention.

By "operably linked" or "operably associated" as used herein, it is meant that the indicated elements are functionally related to each other, and are also generally physically related. For example, a promoter is operatively linked or operably associated to a coding sequence (e.g., nucleotide sequence of interest) if it controls the transcription of the sequence. Thus, the term "operatively linked" or "operably associated" as used herein, refers to nucleotide sequences on a single nucleic acid molecule that are functionally associated. Those skilled in the art will appreciate that the control sequences (e.g., promoter) need not be contiguous with the coding sequence, as long as they function to direct the expression thereof. Thus, for example, intervening untranslated, yet transcribed, sequences can be present between a promoter and a coding sequence, and the promoter sequence can still be considered "operably linked" to the coding sequence.

By the term "express," "expressing" or "expression" (or other grammatical variants) of a nucleic acid coding sequence, it is meant that the sequence is transcribed. In particular embodiments, the terms "express," "expressing" or "expression" (or other grammatical variants) can refer to both transcription and translation to produce an encoded polypeptide.

"Wild-type" nucleotide sequence or amino acid sequence refers to a naturally occurring ("native") or endogenous nucleotide sequence (including a cDNA corresponding thereto) or amino acid sequence.

The terms "nucleic acid," "polynucleotide" and "nucleotide sequence" are used interchangeably herein unless the context indicates otherwise. These terms encompass both RNA and DNA, including cDNA, genomic DNA, partially or completely synthetic (e.g., chemically synthesized) RNA and DNA, and chimeras of RNA and DNA. The nucleic acid, polynucleotide or nucleotide sequence may be double-stranded or single-stranded, and further may be synthesized using nucleotide analogs or derivatives (e.g., inosine or phosphorothioate nucleotides). Such nucleotides can be used, for example, to prepare nucleic acids, polynucleotides and nucleotide sequences that have altered base-pairing abilities or increased resistance to nucleases. The present invention further provides a nucleic acid, polynucleotide or nucleotide sequence that is the complement (which can be either a full complement or a partial complement) of a nucleic acid, polynucleotide or nucleotide sequence of the invention. Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage.

The nucleic acids and polynucleotides of the invention are optionally isolated. An "isolated" nucleic acid molecule or polynucleotide is a nucleic acid molecule or polynucleotide that, by the hand of man, exists apart from its native environment and is therefore not a product of nature. An isolated nucleic acid molecule or isolated polynucleotide may exist in a purified form or may exist in a non-native environment such as, for example, a recombinant host cell. Thus, for example, the term "isolated" means that it is separated from the chromosome and/or cell in which it naturally occurs. A nucleic acid or polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and polynucleotides of the invention can be considered to be "isolated."

Further, an "isolated" nucleic acid or polynucleotide can be a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. The "isolated" nucleic acid or polynucleotide can exist in a cell (e.g., a plant cell), optionally stably incorporated into the genome. According to this embodiment, the "isolated" nucleic acid or polynucleotide can be foreign to the cell/organism into which it is introduced, or it can be native to the cell/organism, but exist in a recombinant form (e.g., as a chimeric nucleic acid or polynucleotide) and/or can be an additional copy of an endogenous nucleic acid or polynucleotide. Thus, an "isolated nucleic acid molecule" or "isolated polynucleotide" can also include a nucleotide sequence derived from and inserted into the same natural, original cell type, but which is present in a non-natural state, e.g., present in a different copy number, in a different genetic context and/or under the control of different regulatory sequences than that found in the native state of the nucleic acid molecule or polynucleotide.

In representative embodiments, the "isolated" nucleic acid or polynucleotide is substantially free of cellular material (including naturally associated proteins such as histones, transcription factors, and the like), viral material, and/or culture medium (when produced by recombinant DNA techniques), or chemical precursors or other chemicals (when chemically synthesized). Optionally, in representative embodiments, the isolated nucleic acid or polynucleotide is at least about 10%, 20%, 30%, 40%, 50%, 60%, 70%, 80%, 90%, 95% or more pure.

As used herein, the term "recombinant" nucleic acid, polynucleotide or nucleotide sequence refers to a nucleic acid, polynucleotide or nucleotide sequence that has been constructed, altered, rearranged and/or modified by genetic engineering techniques. The term "recombinant" does not refer to alterations that result from naturally occurring events, such as spontaneous mutations, or from non-spontaneous mutagenesis.

A "vector" is any nucleic acid molecule for the cloning of and/or transfer of a nucleic acid molecule or nucleotide sequence into a cell. A vector may be a replicon to which another nucleotide sequence may be attached to allow for replication of the attached nucleotide sequence. A "replicon" can be any genetic element (e.g., plasmid, phage, cosmid, chromosome, minichromosome, viral genome) that functions as an autonomous unit of nucleic acid replication in the cell, i.e., capable of nucleic acid replication under its own control. The term "vector" includes both viral and nonviral (e.g., plasmid) nucleic acid molecules for introducing a nucleic acid into a cell in vitro, ex vivo, and/or in vivo, and is optionally an expression vector. A large number of vectors known in the art may be used to manipulate, deliver and express polynucleotides. Vectors may be engineered to contain sequences encoding selectable markers that provide for the selection of cells that contain the vector and/or have integrated some or all of the nucleic acid of the vector into the cellular genome. Such markers allow identification and/or selection of host cells that incorporate and express the proteins encoded by the marker. A "recombinant" vector refers to a viral or non-viral vector that comprises one or more nucleotide sequences of interest (e.g., transgenes), e.g., two, three, four, five or more nucleotide sequences of interest.

Viral vectors have been used in a wide variety of gene delivery applications in cells, as well as living animal subjects. Plant viral vectors that can be used include, but are not limited to, geminivirus vectors. Non-viral vectors include, but are not limited to, plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (e.g., delivery to specific tissues, duration of expression, etc.).

Two nucleotide sequences are said to be "substantially identical" to each other when they share at least about 60%, 70%, 75%, 80%, 85%, 90%, 95%, 97%, 98%, 99% or even 100% sequence identity.

Two amino acid sequences are said to be "substantially identical" or "substantially similar" to each other when they share at least about 60%, 70%, 75%, 80%, 85%, 90%, 95%, 97%, 98%, 99% or even 100% sequence identity or similarity, respectively.

As used herein "sequence identity" refers to the extent to which two optimally aligned polynucleotide or polypeptide sequences are invariant throughout a window of alignment of components, e.g., nucleotides or amino acids.

As used herein "sequence similarity" or "sequence homology" is similar to sequence identity (as described herein), but permits the substitution of conserved amino acids (e.g., amino acids whose side chains have similar structural and/or biochemical properties), which are well-known in the art.

As is known in the art, a number of different programs can be used to identify whether a nucleic acid has sequence identity or an amino acid sequence has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology*, 266, 460-480 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389-3402 (1997).

The CLUSTAL program can also be used to determine sequence similarity. This algorithm is described by Higgins et al. (1988) *Gene* 73:237; Higgins et al. (1989) *CABIOS* 5:151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331.

The alignment may include the introduction of gaps in the sequences to be aligned. In addition, for sequences which contain either more or fewer nucleotides than the nucleic acids disclosed herein, it is understood that in one embodiment, the percentage of sequence identity will be determined based on the number of identical nucleotides acids in relation to the total number of nucleotide bases. Thus, for example, sequence identity of sequences shorter than a sequence specifically disclosed herein, will be determined using the number of nucleotide bases in the shorter sequence, in one embodiment. In percent identity calculations relative weight is not assigned to various manifestations of sequence variation, such as, insertions, deletions, substitutions, etc.

Two nucleotide sequences can also be considered to be substantially identical when the two sequences hybridize to each other under stringent (i.e., strict) conditions. A non-limiting example of stringent hybridization conditions include conditions represented by a wash stringency of 50% Formamide with 5×Denhardt's solution, 0.5% SDS and 1×SSPE at 42° C. Another nonlimiting example of stringent hybridization conditions includes hybridization and membrane washing in 0.1×SSPE (or 0.1×SSC), 0.1% SDS solution, at 65° C. "Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen Laboratory Techniques in *Biochemistry and Molecular Biology—Hybridization with Nucleic Acid Probes* part I chapter 2 "Overview of principles of hybridization and the strategy of nucleic acid probe assays" Elsevier, New York (1993). In some representative embodiments, two nucleotide sequences considered to be substantially identical hybridize to each other under highly stringent conditions. Generally, highly stringent hybridization and wash conditions are selected to be about 5° C. lower than the thermal melting point ($T_m$) for the specific sequence at a defined ionic strength and pH.

As used herein, the term "polypeptide" encompasses peptides, fragments, and proteins (including fusion proteins), unless indicated otherwise.

A "DT1 protein" or "DT1 polypeptide" as used herein refers to a protein or polypeptide that confers drought tolerance to a plant and comprises, consists of, or consists essentially of an amino acid sequence that is substantially identical or substantially similar to a native DT1 polypeptide (e.g., the polypeptide of SEQ ID NO: 1).

The polypeptides of the invention are optionally "isolated." An "isolated" polypeptide is a polypeptide that, by the hand of man, exists apart from its native environment and is therefore not a product of nature. An isolated polypeptide may exist in a purified form or may exist in a non-native environment such as, for example, a recombinant host cell. The recombinant polypeptides of the invention can be considered to be "isolated."

In representative embodiments, an "isolated" polypeptide means a polypeptide that is separated or substantially free from at least some of the other components of the naturally occurring organism or virus, for example, the cell or viral structural components or other polypeptides or nucleic acids commonly found associated with the polypeptide. In particular embodiments, the "isolated" polypeptide is at least about 1%, 5%, 10%, 25%, 50%, 60%, 70%, 75%, 80%, 85%, 90%, 95%, 97%, 98%, 99% or more pure (w/w). In other embodiments, an "isolated" polypeptide indicates that at least about a 5-fold, 10-fold, 25-fold, 100-fold, 1000-fold, 10,000-fold, or more enrichment of the protein (w/w) is achieved as compared with the starting material. In representative embodiments, the isolated polypeptide is a recombinant polypeptide produced using recombinant nucleic acid techniques.

A "biologically active" polypeptide is one that substantially retains at least one biological activity normally associated with the wild-type polypeptide. In particular embodiments, the "biologically active" polypeptide substantially retains all of the biological activities possessed by the unmodified (e.g., native) sequence. By "substantially retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide).

A polypeptide having "DT1 protein activity" or "DT1 polypeptide activity" confers drought tolerance when introduced into a plant. In representative embodiments, the polypeptide retains at least about 50%, 60%, 75%, 85%, 90%, 95%, 97%, 98%, 99%, or more of the activity of a native DT1 protein (e.g., the amino acid sequence of SEQ ID NO: 1) in conferring drought tolerance to a plant (and can even have a higher level of activity than the native DT1 protein).

"Introducing" in the context of a plant cell, plant tissue, plant part and/or plant means contacting a nucleic acid molecule with the plant cell, plant tissue, plant part, and/or plant in such a manner that the nucleic acid molecule gains access to the interior of the plant cell or a cell of the plant tissue, plant part or plant. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol.

The term "transformation" as used herein refers to the introduction of a heterologous and/or isolated nucleic acid into a cell. Transformation of a cell may be stable or transient. Thus, a transgenic plant cell, plant tissue, plant part and/or plant of the invention can be stably transformed or transiently transformed.

"Transient transformation" in the context of a polynucleotide means that a polynucleotide is introduced into the cell and does not integrate into the genome of the cell.

As used herein, "stably introducing," "stably introduced," "stable transformation" or "stably transformed" (and similar terms) in the context of a polynucleotide or nucleic acid molecule introduced into a cell, means that the introduced polynucleotide or nucleic acid molecule is stably integrated into the genome of the cell (e.g., into a chromosome or as a stable-extra-chromosomal element). As such, the integrated polynucleotide or nucleic acid molecule is capable of being inherited by progeny cells and plants.

"Genome" as used herein includes the nuclear and/or plastid genome, and therefore includes integration of a polynucleotide into, for example, the chloroplast genome. Stable transformation as used herein can also refer to a polynucleotide that is maintained extrachromosomally, for example, as a minichromosome.

As used herein, the terms "transformed" and "transgenic" refer to any plant, plant cell, plant tissue (including callus), or plant part that contains all or part of at least one recombinant or isolated nucleic acid molecule, polynucleotide or nucleotide sequence. In representative embodiments, the recombinant or isolated nucleic acid, polynucleotide or nucleotide sequence is stably integrated into the genome of the plant (e.g., into a chromosome or as a stable extra-chromosomal element), so that it is passed on to subsequent generations of the cell or plant.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, and guard cells, cuticle, mesophyll cells; callus tissue; and cuttings. The term "plant part" also includes plant cells, including plant cells that are intact in plants and/or parts of plants, plant protoplasts, plant tissues, plant organs plant cell tissue cultures, plant calli, plant clumps, and the like. As used herein, "shoot" refers to the above ground parts including the leaves and stems.

The term "tissue culture" encompasses cultures of tissue, cells, protoplasts and callus.

As used herein, "plant cell" refers to a structural and physiological unit of the plant, which typically comprises a cell wall but also includes protoplasts. A plant cell of the present invention can be in the form of an isolated single cell or can be a cultured cell or can be a part of a higher-organized unit such as, for example, a plant tissue (including callus) or a plant organ.

Any plant (or groupings of plants, for example, into a genus or higher order classification) can be employed in practicing the present invention including angiosperms or gymnosperms, monocots or dicots.

Exemplary plants include, but are not limited to, corn (*Zea mays*), canola (*Brassica napus, Brassica rapa* ssp.), alfalfa (*Medicago saliva*), rice (*Oryza sativa*, including without limitation *Indica* and/or *Japonica* varieties), sugar cane (*Saccharum* spp.), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*). duckweed (*Lemna*), oats (*Avena sativa*), barley (*Hordium vulgare*), vegetables, ornamentals, conifers, and turfgrasses (e.g., for ornamental, recreational or forage purposes), and biomass grasses (e.g., switchgrass and *miscanthus*).

Vegetables include, but are not limited to, Solanaceous species (e.g., tomatoes; *Lycopersicon esculentum*), lettuce (e.g., *Lactuea sativa*), carrots (*Caucus carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. Hubbard*), Butternut squash (*C. moschata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana,* and *C. martinezii,* and members of the genus *Cucumis* such as cucumber (*Cucumis sativus*), cantaloupe (*C. cantalupensis*), and musk melon (*C. melo*).

Ornamentals include, but are not limited to, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*dianthus caryophyllus*), poinsettia (*Euphorbia pulcherima*), and *chrysanthemum*.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include, but are not limited to, *zoysia* grasses, bent grasses, fescue grasses, blue grasses, St. Augustine grasses, Bermuda grasses, buffalo grasses, rye grasses, and orchard grasses.

Also included are plants that serve primarily as laboratory models, e.g., *Arabidopsis* species.

In representative embodiments, the plant of the invention is exposed to drought or is at risk for exposure to drought.

The term "transformation" as used herein refers to the introduction of a heterologous or exogenous nucleic acid molecule into a cell. Transformation of a cell may be stable or transient. The term "transient transformation" or "transiently transformed" refers to the introduction of one or more heterologous nucleic acid molecules into a cell wherein the heterologous nucleic acid molecule is not heritable from one generation to another.

"Stable transformation" or "stably transformed" refers to the integration of the heterologous nucleic acid molecule into the genome of the plant or incorporation of the heterologous nucleic acid molecule into the cell or cells of the plant (e.g., via a plasmid) such that the heterologous nucleic acid molecule is heritable across repeated generations. Thus, in one embodiment of the present invention a stably transformed plant is produced.

Transient transformation may be detected by, for example, an enzyme-linked immunosorbent assay (ELISA) or Western blot, which can detect the presence of a peptide or polypeptide encoded by one or more transgene introduced into a plant. Stable transformation of a cell can be detected by, for example, a Southern blot hybridization assay of genomic DNA of the cell with nucleic acid sequences which specifically hybridize with a nucleotide sequence of a transgene introduced into a plant. Stable transformation of a cell can be detected by, for example, a Northern blot hybridization assay of RNA of the cell with nucleic acid sequences which specifically hybridize with a nucleotide sequence of a transgene introduced into a plant. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

A nucleic acid molecule or vector of this invention can be introduced into a plant cell by any method known to those of skill in the art. Procedures for transforming a wide variety of plant species are well known and routine in the art and described throughout the literature. Such methods include, but are not limited to, transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Bacterial mediated nucleic acid delivery includes but is not limited to DNA delivery by *Agrobacterium* spp. and is described, for example, in Horsch et al. (*Science* 227:1229 (1985); Ishida et al. (*Nature Biotechnol.* 14:745 750 (1996); and Fraley et al. (*Proc. Natl. Acad. Sci.* 80: 4803 (1983)). Transformation by various other bacterial species is described, for example, in Broothaerts et al. (*Nature* 433: 629-633 (2005)).

Physical delivery of nucleotide sequences via microparticle bombardment is also well known and is described, for example, in Sanford et al. (*Methods in Enzymology* 217: 483-509 (1993)) and McCabe et al. (*Plant Cell Tiss. Org. Cult.* 33:227-236 (1993)).

Another method for physical delivery of nucleic acid to plants is sonication of target cells. This method is described, for example, in Zhang et al. (*Bio/Technology* 9:996 (1991)). Nanoparticle-mediated transformation is another method for delivery of nucleic acids into plant cells (Radu et al., *J. Am. Chem. Soc.* 126: 13216-13217 (2004); Torney, et al. *Society for In Vitro Biology*, Minneapolis, Minn. (2006)). Alternatively, liposome or spheroplast fusion can be used to introduce nucleotide sequences into plants. Examples of the use of liposome or spheroplast fusion are provided, for example, in Deshayes et al. (*EMBO J.*, 4:2731 (1985), and Christou et al. (*Proc Natl. Acad. Sci. U.S.A.* 84:3962 (1987)). Direct uptake of nucleic acid into protoplasts using $CaCl_2$ precipitation, polyvinyl alcohol or poly-L-ornithine is described, for example, in Hain et al. (*Mol. Gen. Genet.* 199:161 (1985)) and Draper et al. (*Plant Cell Physiol.* 23:451 (1982)). Electroporation of protoplasts and whole cells and tissues is described, for example, in Donn et al. (In *Abstracts of VIIth International Congress on Plant Cell and Tissue Culture IAPTC*, A2-38, p 53 (1990); D'Halluin et al. (*Plant Cell* 4:1495-1505 (1992)); Spencer et al. (*Plant Mol. Biol.* 24:51-61 (1994)) and Fromm et al. (*Proc. Natl. Acad. Sci.* 82: 5824 (1985)). Polyethylene glycol (PEG) precipitation is described, for example, in Paszkowski et al. (*EMBO J.* 3:2717 2722 (1984)). Microinjection of plant cell protoplasts or embryogenic callus is described, for example, in Crossway (*Mol. Gen. Genetics* 202:179-185 (1985)). Silicon carbide whisker methodology is described, for example, in Dunwell et al. (*Methods Mol. Biol.* 111:375-382 (1999)); Frame et al. (*Plant J.* 6:941-948 (1994)); and Kaeppler et al. (*Plant Cell Rep.* 9:415-418 (1990)).

In addition to these various methods of introducing nucleic acid molecules into plant cells, expression vectors and in vitro culture methods for plant cell or tissue transformation and regeneration of plants are also well known in the art and are available for carrying out the methods of this invention. See, for example, Gruber et al. ("Vectors for Plant Transformation" in *Methods in Plant Molecular Biology and Biotechnology*, Glick, B. R. and Thompson, J. E., Eds. (CRC Press, Inc., Boca Raton, (1993), pages 89-119).

A plant cell of this invention can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

A large variety of plants have been shown to be capable of regeneration from transformed individual cells to obtain transgenic plants. Those of skill in the art can optimize the particular conditions for transformation, selection and regeneration according to these art-known methods. Factors that affect the efficiency of transformation include the species of plant, the tissue infected, composition of the medium for tissue culture, selectable marker coding sequences, the length of any of the steps of the methods described herein, the kinds of vectors, and/or light/dark conditions. Therefore, these and other factors can be varied to determine the optimal transformation protocol for any particular plant species. It is recognized that not every species will react in the same manner to the transformation conditions and may require a slightly different modification of the protocols disclosed herein. However, by altering each of the variables according to methods routine in the art, an optimum protocol can be derived for any plant species.

Accordingly, in one embodiment, a heterologous nucleotide sequence is introduced into a cell of a plant of the present invention by co-cultivation of the cell with *Agrobacterium tumefaciens* to produce a transgenic plant. In a further embodiment, a heterologous nucleotide sequence is introduced into a cell of a plant of the present invention by direct nucleic acid transfer to produce a transgenic plant.

The recombinant expression vector containing said gene can be constructed using an existing plant expression vector. Said plant expression vector comprises binary *Agrobacterium* vector and vector applicable for plant microprojectile bombardment, etc. Said plant expression vector can also comprise nontranslational region at the 3' end of the exogenous gene, i.e. DNA fragment containing polyadenylic acid signal and any other that is involved in mRNA processing or gene expression. Said polyadenylic acid signal can guide polyadenylic acids adding to the 3' end of the mRNA precursor. When the recombinant plant expression vector is constructed using said gene, any enhanced promoter or constitutive promoter can be added ahead of the transcription initiation nucleotides thereof, which can be used alone or in combination with other plant promoters; in addition, when plant expression vector is constructed using the gene of the present invention, enhancer can also be used, including translational enhancer or transcriptional enhancer, wherein these enhancer regions can be ATG initiation codon or adjacent region initiation codon, etc, however these enhancer regions must be in the same reading frame as the coding sequence so as to guarantee correct translation of the whole sequence. The sources of said translation control signal and initiation codon are extensive, which can be natural or synthetic. The translation initiation region can be originated from the transcription initiation region or structural genes. In order to facilitate identification and screening of the transgenic plant cells or plants, the applied plant expression vector can be processed, for example, added with genes expressed in plants and encoded enzymes producing color change or luminescent compounds, genes of resistant antibiotic markers or chemical agent resistant markers, and the like. Also, the transformed strains can be directly screened through stress without adding any selective marker genes.

By "enhanced drought tolerance" or "increased drought tolerance" is meant that the transgenic plant of this invention recovers, thrives, survives and/or overcomes drought conditions better than a control plant lacking the nucleic acid molecule or vector of this invention, maintained under and/or subjected to identical conditions. In various embodiments, the transgenic plant can have about 10%, about 20%, about 30%, about 40%, about 50% about 60%, about 70%, about 80%, about 90% or about 100% enhancement in or increase in tolerance to drought conditions as compared with the control plant.

A nonlimiting example of a rice drought tolerant line is IL23, which is publicly available from China Agriculture University (Zhang et al. "Identification of a drought tolerant introgression line derived from Dongxiang common wild rice (*O. rufipogon* Griff.)" *Plant Mol Biol* 2006, 62:247-259).

The *Japonica* rice cultivar Nipponbare is available from the National Seed Resource Library, under Library No. I1A13071.

The plant expression vector Super1300 is publicly available from China Agriculture University (designated as "pCAMBIA 1300" in Yang et al. "Overexpression of SOS (Salt Overly Sensitive) Genes Increases Salt Tolerance in Transgenic *Arabidopsis*" *Molecular Plant* 2009, 2:22-31).

Polypeptides and Nucleic Acid Molecules of the Invention

In some embodiments of the present invention, an isolated polypeptide is provided comprising, consisting essentially of, or consisting of an amino acid sequence selected from the group consisting of: a) the amino acid sequence of SEQ ID NO:1; b); a fragment of at least about 10, 15, 25, 50, 75, 100, 125, 150, 175, 200 or more contiguous amino acids of the amino acid sequence of SEQ ID NO:1, wherein the fragment has DT1 protein activity; c) an amino acid sequence of a naturally occurring allelic variant of a DT1 protein having the amino acid sequence of SEQ ID NO:1; and d) an amino acid sequence having at least 80% identity (e.g., 50%, 60%, 70%, 80%. 90%, 95%, 97%, 98%, 99% identity) with the amino acid sequence of any of (a)-(c) above.

In representative embodiments, the DT1 protein or fragment is a fusion protein. For example, in some embodiments, in order to facilitate purification of the protein, polypeptide or fragment of this invention, the amino terminal or carboxyl terminal of the protein, polypeptide or fragment of this invention can be linked with one or more (e.g., 2, 3, 4, 5, etc.) of the tags shown in Table 1.

TABLE 1

| Tag | Residue | Sequence |
|---|---|---|
| Poly-Arg | 5-6 (normally 5) | RRRRR (SEQ ID NO: 4) |
| Poly-His | 2-10 (normally 6) | HHHHHH (SEQ ID NO: 5) |
| FLAG | 8 | DYKDDDDK (SEQ ID NO: 6) |
| Strep-tag II | 8 | WSHPQFEK (SEQ ID NO: 7) |
| c-myc | 10 | EQKLISEEDL (SEQ ID NO: 8) |

The protein of this invention can be modified by substitution, deletion and/or addition of one or more of the amino acid residues of the amino acid sequence of SEQ ID NO:1, while retaining the function of being associated with plant drought tolerance. Such a modified protein can either be artificially synthesized or can be obtained by firstly synthesizing its coding nucleotide sequence and then carrying out biological expression. The coding nucleotide sequence of the modified protein of this invention can be obtained by deleting one or several codons in the nucleotide sequence of SEQ ID NO:2, and/or by carrying out missense mutations of one or several base pairs, and/or linking the coding sequence to one or more of the tags as shown in Table 1 at the 5' end and/or the 3' end.

The present invention further provides a nucleic acid molecule (e.g., an isolated nucleic acid molecule) selected from the group consisting of a) the nucleotide sequence of SEQ ID NO:2; b) a nucleotide sequence that encodes the amino acid sequence of SEQ ID NO:1; c) a nucleotide sequence that encodes at least 15 contiguous amino acids of the amino acid sequence of SEQ ID NO:1; d) a nucleotide sequence having at least about 80% identity (e.g., at least about 50%, 60%, 70%, 80%, 90%, 95%, 97%, 98% or 99% identity) with the nucleotide sequence of SEQ ID NO:2 and that encodes a DT1 protein; e) a nucleotide sequence that encodes a naturally occurring allelic variant of a polypeptide having the amino acid sequence of SEQ ID NO:1; f) a nucleotide sequence that encodes an amino acid sequence having at least 80% identity (e.g., at least about 50%, 60%, 70%, 80%, 90%, 95%, 97%, 98% or 99% identity) with the amino acid sequence of SEQ ID NO:1 and is a DT1 protein; g) a nucleotide sequence consisting of or consisting essentially of nucleotides 59 through 481 of the nucleotide sequence of SEQ ID NO:2; h) a nucleotide sequence consisting of or consisting essentially of nucleotides 19 through 641 of the nucleotide sequence of SEQ ID NO:2; i) a nucleotide sequence that differs from the nucleotide sequence of (a)-(f), above due to the degeneracy of the genetic code and that encodes a DT1 protein; and g) a nucleotide sequence that hybridizes with the complement (e.g., the complete complement) of the nucleotide sequence of (a)-(i) above under stringent conditions.

In some embodiments, the nucleic acid molecule of this invention can comprise a nucleotide sequence operably associated with a promoter.

Further provided herein is a vector comprising the nucleic acid molecule of this invention, which can be, for example the plant expression vector Super1300. The plant expression vector Super1300 is publicly available from China Agriculture University (designated as "pCAMBIA 1300" in Yang et al. "Overexpression of SOS (Salt Overly Sensitive) Genes Increases Salt Tolerance in Transgenic *Arabidopsis*" *Molecular Plant* 2009, 2:22-31).

The present invention additionally provides a cell comprising a polypeptide, nucleic acid molecule and/or vector of this invention. In some embodiments, the cell can be a plant cell. In further embodiments the nucleic acid molecule and/or vector of this invention can be stably integrated into the genome of the cell. Additional embodiments of this invention include a plant part comprising a plant cell of this invention.

In yet further embodiments, the present invention provides a transgenic plant comprising a plant cell of this invention, as well as a stably transformed plant comprising a nucleic acid molecule of this invention or a vector of this invention incorporated into its genome.

Also provided herein is a product harvested from a plant of this invention, as well as a processed product produced from a harvested product of this invention.

The present invention further provides a transformed plant cell comprising a nucleic acid molecule or a multiplicity of different nucleic acid molecules of this invention, in any combination. Furthermore, the elements of the nucleic acid molecules transformed into the plant cell can be in any combination.

A transgenic plant is also provided herein, comprising, consisting essentially of and/or consisting of one or more nucleic acid molecules of this invention. A transgenic plant is additionally provided herein comprising a transformed plant cell of this invention.

Additionally provided herein is a transgenic seed, a transgenic pollen grain and a transgenic ovule of the transgenic plant of this invention. A further aspect of this invention includes a seed comprising a nucleic acid molecule of this invention or a vector of this invention incorporated into its genome. Further provided is a tissue culture of regenerable transgenic cells of the transgenic plant of this invention.

In some embodiments, the plant of this invention is a crop plant. Thus, in one embodiment of this invention, a crop of plants is provided, comprising, consisting essentially of or consisting of a plurality of plants of this invention, e.g., planted together in an agricultural field.

In additional embodiments, the present invention provides primers and primer pairs for amplification of the nucleic acid molecules of this invention. In some embodiments a primer pair is provided for amplifying the total length or any fragment of a nucleic acid molecule of this invention. Nonlimiting examples of primers and primer pairs of this invention include:

```
S12F:
5'-AGAACCCCCAACCTAACCGGCTGCAG-3'
(SEQ ID NO: 9, carrying PstI enzyme cleav-
age recognition
sequence);

S12R:
5'-GGACTAGTCTCTAATGCTGCCTCCAGATCAC-3'
(SEQ ID NO: 10, carrying SpeI enzyme cleav-
age recognition
sequence);

S12-1F:
5'-GCCACCAAGCTAAATGCACTGC-3' (SEQ ID NO: 11);

S12-1R:
5'-CTCTAATGCTGCCTCCAGATCAC-3' (SEQ ID NO: 12);

F1:
5'-TACTTCTACACAGCCATC-3' (SEQ ID NO: 13);
and

R1:
5'-CGTCTGTCGAGAAGTTTC-3' (SEQ ID NO: 14).
```

Methods of Use

The present invention also provides a method for producing transgenic plants, in which a nucleic acid molecule of this invention is introduced into a target plant so as to obtain a transgenic plant with increased (e.g., enhanced) drought tolerance as compared with a target plant lacking the nucleic acid molecule of this invention. Thus, in one embodiment, the present invention provides a method of producing a transgenic plant having increased drought tolerance, comprising introducing a nucleic acid molecule and/or a vector of this invention into a cell of a plant under conditions whereby the nucleic acid molecule is expressed to produce a DT1 polypeptide, thereby producing a transgenic plant having enhanced or increased drought tolerance.

In particular embodiments, the method comprises: (a) introducing a nucleic acid (e.g., isolated nucleic acid) and/or vector of this invention encoding a DT1 polypeptide into a plant cell (including a callus cell) to produce a transgenic plant cell; and (b) regenerating a transgenic plant from the transgenic plant cell of (a), optionally wherein the transgenic plant comprises in its genome the nucleic acid and/or vector and, as a further option, has increased (e.g., enhanced) drought tolerance as compared with a control plant lacking the nucleic acid and/or vector of this invention (e.g., expresses the nucleic acid and/or vector to produce a DT1 polypeptide in an amount effective to enhance drought tolerance in the plant).

In additional embodiments, the method comprises: (a) introducing a nucleic acid (e.g., isolated nucleic acid) and/or vector of this invention encoding a DT1 polypeptide into a plant cell (including a callus cell) to produce a transgenic plant cell; and (b) regenerating a transgenic plant from the transgenic plant cell of (a), optionally wherein the transgenic plant comprises in its genome the nucleic acid and/or vector; and (c) selecting from a plurality of the transgenic plants of (b) a transgenic plant having increased drought tolerance (e.g., the transgenic plant expresses the nucleic acid and/or vector and produces a DT1 polypeptide in an amount effective to increase drought tolerance in the plant).

Optionally, the methods of the invention can further comprise exposing the plant, plant part or plant cell to drought conditions.

In representative embodiments, the methods are practiced with a plant exposed to drought or at risk for exposure to drought.

The invention also contemplates the production of progeny plants that comprise a nucleic acid (e.g., an isolated nucleic acid) and/or vector of this invention encoding a DT1 polypeptide. In embodiments of the invention, the method further comprises obtaining a progeny plant derived from the transgenic plant (e.g., by sexual reproduction or vegetative propagation). Optionally the progeny plant comprises in its genome an isolated nucleic acid and/or vector encoding a DT1 polypeptide and has increased drought tolerance as compared with a control plant lacking the nucleic acid molecule and/or vector of this invention (e.g., expresses the nucleic acid and/or vector and produces a DT1 polypeptide in an amount effective to increase drought tolerance in the plant).

To illustrate, in one embodiment, the invention provides a method of producing a progeny plant, the method comprising (a) crossing the transgenic plant comprising the nucleic acid (e.g., isolated nucleic acid) and/or vector of this invention encoding a DT1 polypeptide with itself or another plant to produce seed comprising the nucleic acid and/or vector; and (b) growing a progeny plant from the seed to produce a transgenic plant, optionally wherein the progeny plant comprises in its genome the nucleic acid and/or vector encoding a DT1 polypeptide and has increased drought tolerance as compared with a control plant that lacks a nucleic acid and/or vector of this invention (e.g., expresses the nucleic acid and/or vector and produces the DT1 polypeptide in an amount effective to increase drought tolerance in the plant). In additional embodiments, the method can further comprise (c) crossing the progeny plant with itself or another plant and (d) repeating steps (b) and (c) for an additional 0-7 (e.g., 0, 1, 2, 3, 4, 5, 6 or 7 and any range thereof) generations to produce a plant, optionally wherein the plant comprises in its genome the nucleic acid and/or vector encoding a DT1 polypeptide and has increased drought tolerance (e.g., expresses the nucleic acid and/or vector and expresses the DT1 polypeptide in an amount effective to increase drought tolerance in the plant).

According to the present invention, the nucleic acid molecule and/or vector can be specifically transferred into a target plant, plant cell or plant tissue through, for example, a recombinant expression vector. A nucleic acid molecule and/or a vector carrying said nucleic acid molecule can be transformed into plant cells or tissues through conventional biological methods such as, e.g., Ti-plasmid, Ri-plasmid, plant virus vector, direct DNA transformation, microinjection, electrotransformation, *Agrobacterium* mediation, gene gun, etc., and the transformed plant tissues can be cultivated into strains. The target plant can be either a monocotyledon or a dicotyledon. A nonlimiting example of a monocotyledon can be rice, such as, e.g., *Japonica* rice cultivar Nipponbare. In some embodiments, said drought tolerance is drought tolerance in exhibited in the seedling stage.

The method for producing a drought tolerant plant according to the present invention has important theoretical and practical significance in the study of molecular mechanisms of plant drought tolerance, selection of drought tolerant plant species and molecular breeding of plant drought tolerance, which provides an economic, quick and effective pathway for increasing drought tolerance of plants. The present invention will have extensive application and market prospects in the agricultural field.

EXAMPLES

The following examples are provided for better understanding of the present invention but not limiting of the present invention. The experimental methods described herein are conventional methods, unless specially stated. The test materials used in the following example, unless specially stated, are all commercially available from normal biochemical reagent shops (analytically pure). The quantitative tests in the following examples are all set forth with triplicate experiments and the results are the average values thereof. The primer synthesis and sequencing was done by Beijing AuGCT DNA-SYN Biotechnology Co., Ltd.

Example 1. Discovery of Drought Tolerance Associated Protein DT1 and Gene Thereof Rice drought tolerance line IL23 and the control parent Guichao 2 were used as materials for chip hybridization (the chip was the GeneChip® Rice Genome Array from Affimetrix Corporation, Product No.: 900599), and analyzed on the basis of chip data analysis and in combination with comparative genomics, the drought tolerance associated gene was screened. Finally a new drought tolerant gene was identified through genomic comparison and correlation analysis of drought tolerance; under condition of 30% PEG treating, the expression level of the gene was significantly increased, demonstrating a drought induced gene.

The protein having the amino acid sequence of SEQ ID NO:1 was named DT1 protein (constituted of 140 amino acid residues). The nucleic acid sequence encoding the DT1 protein was named the DT1 gene, the coding sequence of which is provided as SEQ ID NO:2 (constituted of 693 nucleotides; the open reading frame is from nucleotide 59 through nucleotide 481 at the 5' end of the nucleotide sequence of SEQ ID NO:2), and whose genome sequence is provided as SEQ ID NO:3 (constituted of 3275 nucleotides; reverse transcription; having 3 exons and 2 introns).

Example 2. Production and Identification of Transgenic Rice

Construction of Recombinant Plasmid Super1300-DT1 (DT1 Plant Over-Expression Vector)

1) Design of specific primer pair. According to the full-length cDNA sequence of *Japonica* rice cultivar Nipponbare LOC_Os02g06779, the primers were designed and the restriction enzyme PstI and SpeI recognition sites and protective bases were introduced respectively at both ends of the primer and the primer sequences (enzyme cleavage recognition sequence and protective base marked by underlines) were as follows:

```
S12F:
5'-AGAACCCCCAACCTAACCGGCTGCAG-3'
(SEQ ID NO: 9, carrying PstI enzyme cleav-
age recognition sequence);
and S12R:
5'-GGACTAGTCTCTAATGCTGCCTCCAGATCAC-3'
(SEQ ID NO: 10, carrying SpeI enzyme cleav-
age recognition sequence).
```

2) The rice drought tolerance line IL23 strain in the seedling stage was treated by irrigating roots with 30% PEG solution (a mixture by volume of 3 parts polyethylene glycol and 7 parts water; and the degree of polymerization of polyethylene glycol being 6000) for 2 h (20 ml for each strain), and then total RNA was extracted.

3) The total RNA extracted in step 2 was used as a template and SuperScriptII reverse transcriptase (Invitrogen, Cat no. 18064-014) was used to carry out reverse transcription to obtain cDNA.

4) The cDNA obtained in step 3 was used as a template and the primer pair designed in step 1 (S12F and S12R) was used to carry out a PCR amplification, and the purified PCR amplification products (around 623 bp) were recovered.

5) A double enzyme cleavage of the PCR amplification products in step 4 was performed using restriction endonucleases PstI and SpeI so as to obtain the enzyme cleavage products.

6) A double enzyme cleavage of the plant expression vector Super1300 was performed using restriction endonucleases PstI and SpeI to recover the vector backbone (around 9700 bp).

7) The enzyme cleavage products in step 5 and the vector backbone in step 6 were linked to obtain a recombinant plasmid Super1300-DT1.

According to sequencing results, the structure of the recombinant plasmid Super1300-DT1 was described as follows: Super1300 vector was used as the backbone vector, and the DT1 nucleic acid sequence from nucleotide 19 to nucleotide 641 of the nucleotide sequence of SEQ ID NO:2 was inserted between the PstI and SpeI enzyme cleavage sites, and the expression of said DT1 gene is initiated by the super promoter (i.e., 3 octopine synthase enhancers in front of the manopine synthase promoter). Those skilled in the art will appreciate that for the construction of the recombinant plasmid Super1300-DT1, the DT1 nucleic acid sequence from nucleotide 19 to nucleotide 641 of the nucleotide sequence of SEQ ID NO:2 can also be artificially synthesized, optionally, incorporating artificial and/or modified nucleotides.

Production of DT1 Transgenic Rice

1) Obtaining DT1 transgenic rice. The recombinant plasmid Super1300-DT1 was transformed into the matured embryo callus of *Japonica* rice cultivar Nipponbare by a gene gun method and NB culture medium containing 50 mg/L of hygromycin was used to screen for 2 cycles, with each cycle screening for 20-30 days, and a positive strain was obtained through pre-differentiation and differentiation (T0 generation).

In order to avoid interference by endogenous DT1 gene of *Japonica* rice cultivar Nipponbare, a pair of cross-intron primers (constituted of S 12-1F and S 12-1R) were designed according to the sequences of genome and cDNA and a pair of hygromycin primers was designed (constituted of F1 and R1).

```
S12-1F:
5'-GCCACCAAGCTAAATGCACTGC-3' (SEQ ID NO: 11);
and

S12-1R:
5'-CTCTAATGCTGCCTCCAGATCAC-3' (SEQ ID NO: 12).

F1:
5'-TACTTCTACACAGCCATC-3' (SEQ ID NO: 13);

R1:
5'-CGTCTGTCGAGAAGTTTC-3' (SEQ ID NO: 14).
```

The target sequences of 512-1F and 512-1R were the nucleotides from position 248 to position 641 of SEQ ID NO2 and due to the presence of introns, the genome DNA of *Japonica* rice cultivar Nipponbare cannot be amplified when used as a template. The target sequences of F1 and R1 were in the hygromycin resistance coding sequence on the Super1300 vector (around 1000 bp).

The genome DNAs were respectively extracted from the positive strains (T0 generation) obtained from differentiation and were identified by PCR using the DT1 gene primer pairs (512-1F and 512-1R) and the hygromycin primer pairs (F1 and R1), respectively to obtain 40 transgenic strains, wherein the transgenic strains were named S12-1.

2) Producing empty vector transformed rice. The plant expression vector Super1300 was transformed into matured embryo callus of *Japonica* rice cultivar Nipponbare by a gene gun method and NB culture medium containing 50 mg/L of hygromycin was used to screen for 2 cycles, with each cycle screening for 20-30 days; and a positive strain was obtained through pre-differentiation and differentiation (T0 generation).

The genome DNAs were respectively extracted from the positive strains (T0 generation) obtained from differentiation and were identified by PCR using the hygromycin primer pairs (F1 and R1) to obtain 50 empty vector transformed strains, wherein the empty vector transformed strains were named 1300.

3) Comparison of expression level of DT1 gene. The total RNAs of the leaves of the transgenic strain S12-1 (10 strains) and the empty vector transformed strain 1300 (10 strains) were respectively extracted and inverse transcribed into cDNAs; and real-time fluorescence PCR identification was carried out using the cDNAs as templates and the primer pair 512-1F and 512-1R to compare the expression level of the DT1 sequence. Taking the expression level of the DT1 sequence in the empty vector transformed strain 1300 as 1, the expression level of the DT1 sequence in the transgenic strain S12-1 was calculated and the average value was obtained. For the expression level of the DT1 gene in the leaf, the transgenic strain S12-1 was significantly higher than the empty vector transformed strain 1300, which is around 33 times as high as that in the empty vector transformed strain 1300. Triplicate experiments were carried out, and the results were consistent.

4) Phenotypic identification (PEG treating). The T0 generation transgenic strain S12-1 (10 strains), T0 generation empty vector transformed strain 1300 (10 strains) and wild type *Japonica* rice cultivar Nipponbare (10 strains) were respectively treated with PEG at the stage of two leaves and one core, i.e., each plant root was irrigated with 20 ml 30% PEG solution (a mixture by volume of 3 parts polyethylene glycol and 7 parts water and the degree of polymerization of polyethylene glycol being 6000) per day. After 3 d continuous treating, their phenotypes were observed and photographs were taken and infrared detection carried out; after treating with PEG for 3 d, the same were subjected to rewatering treatment, and after rewatering for 5 h (5 h) and rewatering for 2 d (2 d), their respective phenotypes were observed and photographed.

After treating with PEG for 3 days, the phenotypes of the transgenic strains were observed to be consistent. The phenotypes of the empty vector transformed strains were also observed to be consistent. The phenotypes of 10 strains of wild type *Japonica* rice cultivar Nipponbare were consistent. The second leaf of the transgenic strain was curled and only appeared yellowish at the leaf apex, while there was no change in the first leaf. However, the second leaves of the empty vector transformed strain and the wild type *Japonica* rice cultivar Nipponbare were completely curled and the yellowish parts had developed to the middle of the leaves, and wilting was present in the first leaves. There were no significant differences between the phenotypes of the empty vector transformed strain and the wild type *Japonica* rice cultivar Nipponbare.

The infrared detection results of the 1 strain of the transgenic strain and 1 strain of the empty vector transformed strain were analyzed. The phenotypes of the other 9 strains of the transgenic strains were consistent with that of the transgenic strain. The phenotypes of the other 9 strains of the empty vector transformed strains were consistent with that of the empty vector transformed strain. The phenotypes of the 10 strains of the wild type *Japonica* rice cultivar Nipponbare were all consistent. The leaf surface temperature of the transgenic strain was higher than that of the empty vector transformed strain and the wild type *Japonica* rice cultivar Nipponbare, and there were no significant differences between the leaf surface temperatures of the empty vector transformed strain and the wild type *Japonica* rice cultivar Nipponbare.

The phenotypes of other transgenic strains as observed after rewatering for 5 h were consistent. The phenotypes of the empty vector transformed strains were consistent. The phenotypes of the 10 strains of the wild type *Japonica* rice cultivar Nipponbare were all consistent. The originally curled second leaf of the transgenic strain was almost completely expanded, while there were no changes between these of the empty vector transformed strain and the wild type *Japonica* rice cultivar Nipponbare. There were no significant differences between the phenotypes of the empty vector transformed strain and the wild type *Japonica* rice cultivar Nipponbare.

The phenotypes of the transgenic strains observed after rewatering for 2 d were consistent. The phenotypes of the empty vector transformed strains were consistent. The phenotypes of the 10 strains of the wild type *Japonica* rice cultivar Nipponbare were all consistent. The third leaves of most of the transgenic strains grew to around 3 cm, while the second leaves of the empty vector transformed strain and the wild type *Japonica* rice cultivar Nipponbare only expanded by a half and there was growth evidence on their third leaves. There were no significant differences between the phenotypes of the empty vector transformed strain and the wild type *Japonica* rice cultivar Nipponbare. Triplicate experiments were carried out, and the results were consistent.

The results showed that the transgenic strain S12-1 has a lower degree of drought stress than the empty vector transformed strain 1300 and the wild type *Japonica* rice cultivar Nipponbare, and has enhanced drought tolerance; i.e., the drought tolerance of the plant was enhanced by introduction of the DT1 sequence.

5) Phenotypic identification (drought treating). The T0 generation transgenic strain S12-1 (20 strains), T0 generation empty vector transformed strain 1300 (20 strains) and wild type *Japonica* rice cultivar Nipponbare (20 strains) were respectively subjected to drought treatment at the stage of two leaves and one core (i.e., not watering continuously), and subjected to rewatering after 11 days of continuous drought treatment (i.e., recovering the normal watering).

The phenotypes of the transgenic strains were consistent before drought treatment and at the third day of drought treatment. The phenotypes of the empty vector transformed strains were also consistent. The phenotypes of the 20 strains of wild type *Japonica* rice cultivar Nipponbare were all consistent. There were no significant differences among the phenotypes of each strain.

The phenotypes of the transgenic strains at the ninth day of drought treating were consistent. The phenotypes of the empty vector transformed strains were also consistent. The phenotypes of the 20 strains of wild type *Japonica* rice cultivar Nipponbare were all consistent. The leaves of the empty vector transformed strain and the wild type strain were all withered, while for the transgenic strain, there were still uncurled parts of the leaves. There were no significant differences between the phenotypes of the empty vector transformed strain and the wild type *Japonica* rice cultivar Nipponbare.

The phenotypes of the transgenic strains at the second day after rewatering were consistent. The phenotypes of other empty vector transformed strains were consistent. The phenotypes of the 20 strains of wild type *Japonica* rice cultivar Nipponbare were all consistent. The leaves of the empty vector transformed strain and the wild type strain were still all withered, while in the transgenic plant, part of the stains had recovered to grow. There were no significant differences between the phenotypes of the empty vector transformed strain and the wild type *Japonica* rice cultivar Nipponbare. At the $2^{nd}$ day after rewatering, 4 strains of the 20 strains of the transgenic strains recovered to grow, while in both the empty vector transformed strain and the wild type *Japonica* rice cultivar Nipponbare, no strains recovered to grow. Triplicate tests were carried out, and the results were consistent.

The results showed that the transgenic strain S12-1 had a lower degree of drought stress than the empty vector transformed strain 1300 and the wild type *Japonica* rice cultivar Nipponbare, and has enhanced drought tolerance, i.e., the drought tolerance of the plant was enhanced by introduction of the DT1 sequence.

The foregoing is illustrative of the present invention, and is not to be construed as limiting thereof. The invention is defined by the following claims, with equivalents of the claims to be included therein.

All publications, patent applications, patents and other references cited herein are incorporated by reference in their

The invention claimed is:

1. A method for increasing drought tolerance of a plant, comprising introducing a recombinant expression vector comprising a nucleic acid molecule encoding a protein as set forth in SEQ ID NO:1, wherein the nucleic acid molecule is operably associated with a heterologous promoter, into a cell of a target plant under conditions whereby the nucleic acid molecule is expressed, thereby increasing drought tolerance of the target plant as compared with a target plant that does not comprise the nucleic acid molecule encoding the protein as set forth in SEQ ID NO: 1.

2. The method of claim 1, wherein the recombinant expression vector is a plant expression vector Super1200.

3. The method of claim 1, wherein the recombinant expression vector is stably integrated into the genome of the cell.

4. A method for increasing drought tolerance of a plant, comprising regenerating a transgenic plant from a transgenic cell line or plant part comprising a nucleic acid molecule encoding a protein as set forth in SEQ ID NO:1, wherein the nucleic acid molecule is operably associated with a heterologous promoter, thereby increasing drought tolerance of the transgenic plant as compared to a plant that does not comprise the nucleic acid molecule encoding the protein as set forth in SEQ ID NO: 1.

5. A method for increasing drought tolerance of a plant, comprising regenerating a transgenic plant from a transgenic cell line or plant part that comprises a nucleic acid molecule operably associated with a heterologous promoter, wherein the nucleic acid molecule is selected from:
   a. the nucleotide sequence of SEQ ID NO:2;
   b. a nucleotide sequence that encodes the amino acid sequence of SEQ ID NO:1;
   c. a nucleotide sequence consisting of nucleotides 59 through 481 of the nucleotide sequence of SEQ ID NO:2; and
   d. a nucleotide sequence consisting of nucleotides 19 through 641 of the nucleotide sequence of SEQ ID NO:2,
thereby increasing drought tolerance of the transgenic plant as compared to a plant that does not comprise the nucleic acid molecule of (a)-(d) above.

6. A method of increasing drought tolerance of a plant, comprising introducing, into a cell of a target plant, a recombinant expression vector comprising a nucleic acid molecule operably associated with a heterologous promoter, wherein the nucleic acid molecule is selected from:
   a. the nucleotide sequence of SEQ ID NO:2;
   b. a nucleotide sequence that encodes the amino acid sequence of SEQ ID NO:1;
   c. a nucleotide sequence consisting of nucleotides 59 through 481 of the nucleotide sequence of SEQ ID NO:2; and
   d. a nucleotide sequence consisting of nucleotides 19 through 641 of the nucleotide sequence of SEQ ID NO:2,
under conditions whereby the nucleic acid molecule is expressed, thereby increasing drought tolerance of the transgenic plant as compared to a plant that does not comprise the nucleic acid molecule of (a)-(d) above.

7. The method of claim 6, wherein the transgenic plant is a stably transformed plant.

8. The method of claim 6, wherein the plant is a monocotyledon.

9. The method of claim 6, wherein the plant is a dicotyledon.

10. The method of claim 8, wherein the monocotyledon is rice.

11. The method of claim 1, wherein the plant is a dicotyledonous plant or a monocotyledonous plant.

12. The method of claim 11, wherein the monocotyledonous plant is rice.

13. The method of claim 4, wherein the plant is a dicotyledonous plant or a monocotyledonous plant.

14. The method of claim 13, wherein the monocotyledonous plant is rice.

15. The method of claim 5, wherein the plant is a dicotyledonous plant or a monocotyledonous plant.

16. The method of claim 15, wherein the monocotyledonous plant is rice.

* * * * *

UNITED STATES PATENT AND TRADEMARK OFFICE
CERTIFICATE OF CORRECTION

PATENT NO. : 9,879,276 B2  
APPLICATION NO. : 14/116759  
DATED : January 30, 2018  
INVENTOR(S) : Sun et al.

Page 1 of 1

It is certified that error appears in the above-identified patent and that said Letters Patent is hereby corrected as shown below:

On the Title Page

Item (30) Foreign Application Priority Data:
Please correct "2011 1 0119679" to read -- 2011 1 0119679.2 --

Item (30) Foreign Application Priority Data:
Please correct "2011 1 0296327" to read -- 2011 1 0296327.4 --

In the Specification

Column 1, Line 7, Statement of Related Applications, after "This application":
Please insert -- is a 35 U.S.C. § 371 national phase application of International Application Serial No. PCT/CN2012/075230, filed May 9, 2012, which --

Column 22, Line 26:
Please correct "512-1F and 512-1R" to read -- S12-1F and S12-1R --

Column 22, Line 36:
Please correct "(512-1F and 512-1R)" to read -- (S12-1F and S12-1R) --

Column 22, Line 59:
Please correct "512-1F and 512-1R" to read -- S12-1F and S12-1R --

Signed and Sealed this  
Third Day of July, 2018

Andrei Iancu  
*Director of the United States Patent and Trademark Office*